United States Patent [19]

Laganá

[11] Patent Number: 5,306,355
[45] Date of Patent: Apr. 26, 1994

[54] SYSTEM FOR THE PASSIVATION OF METAL SURFACES AFFECTED BY OPERATING CONDITIONS AND AGENTS PROMOTING CORROSION

[75] Inventor: Vincenzo Laganá, Milan, Italy

[73] Assignee: Urea Casale S.A., Lugano, Switzerland

[21] Appl. No.: 846,537

[22] Filed: Mar. 4, 1992

[30] Foreign Application Priority Data

Mar. 18, 1991 [IT] Italy .................. MI 91 A 000715

[51] Int. Cl.$^5$ .................................... C23C 8/12
[52] U.S. Cl. .................................... 148/276; 148/281; 204/129.35
[58] Field of Search ............ 148/270, 271, 240, 276, 148/277, 281, 284; 204/129.35, 140

[56] References Cited

U.S. PATENT DOCUMENTS 5,188,714  2/1993  Davidson et al. .................. 148/276

FOREIGN PATENT DOCUMENTS 0096151  12/1983  European Pat. Off. .
1027202  11/1950  France .

OTHER PUBLICATIONS

Derwent publications, London, gb, nr. 40982c/23, week c23, Jul. 16, 1980 & su-a-44618 (lengd elec eng inst) Oct. 15, 1979, (Abstract).
wpil/derwent, abstract nr. 85-187612 c31, derwent publications, London, gb & jp-a-6-116760 (Hitachi) Jun. 24, 1985, (Abstract).

*Primary Examiner*—Scott Kastler
*Attorney, Agent, or Firm*—Ostrolenk, Faber, Gerb & Soffen

[57] ABSTRACT

A system for the passivation of metal surfaces, and more especially those of stainless steel, titanium, etc., in equipment used for chemical processes, where elements and compounds are formed which have a corrosive action, in particular where temperature and pressure are higher than ambient conditions. In the system the main passivating agent is oxygen (air) combined with at least a second auxiliary agent, characterized by the fact that the latter is ozone (03).

14 Claims, No Drawings

SYSTEM FOR THE PASSIVATION OF METAL SURFACES AFFECTED BY OPERATING CONDITIONS AND AGENTS PROMOTING CORROSION

BACKGROUND OF THE INVENTION

1. Field of the Invention

The present invention relates to a system for the passivation of metal surfaces in equipment affected by operating conditions and by agents which promote corrosion. In general, the present invention relates to a system for the passivation of surfaces in chemical plants involving the presence and formation of corrosive compounds, especially where the environmental conditions, such as temperature and pressure, intensify the corrosive action. More particularly, the present invention concerns a system for the passivation of surfaces of metal equipment used in chemical plants, and exposed to the intensive action of highly corrosive compounds, under temperature and pressure conditions higher than ambient conditions.

2. Description of the Prior Art

It is well known that the synthesis of urea is carried out at high temperature, such as on average 180° to 215° C., and high pressure, such as on average 130 to 400 bar. Provided downstream of the synthesis section are a number of decomposition stages of urea synthesis by-products, i.e., by-products which have not been transformed into urea. Such by-products include ammonium carbamate, which through heat is decomposed into $NH_3$ and $CO_2$, and is separated from the synthesis elements as gaseous $NH_3$ and $CO_2$. The gaseous $NH_3$ and $CO_2$ are condensed in successive condensation stages thereby forming aqueous solutions of ammonium carbamate and/or ammonium carbonate, which are recycled to the synthesis section. The urea is meanwhile concentrated in successive stages operating at decreasing pressure until the final vacuum concentration stage is reached from which virtually pure melted urea is obtained, which is then sent to a finishing stage operated with various techniques.

Various systems have been proposed for the passivation of the equipment used in the respective stages mentioned above, which is subjected to corrosion by the corrosive compounds treated in it. For example, Belgian Patent No. 625.397 describes the use of oxygen as a passivating agent at 180° C. and 270 kg/cm² for the surfaces in a urea synthesis reactor made of stainless steel containing up to 19% Cr and 14% Ni. In general, oxygen can also be replaced by other passivating agents, such as, for example, hydrogen peroxide and alkali metal peroxides or alkali earth peroxides.

In European Patent 0096151, a passivation system is described for strippers, where the effluent from the urea synthesis reactor is treated, at high temperature and a pressure of between 120 and 240 kg/cm², as a thin falling film countercurrent with $NH_3$ or $CO_2$. In this method, to a first passivating agent consisting of an oxygen-containing gas, which is introduced from the bottom of at least one stripper, is added as a second passivating agent a liquid injected from the top of the stripper. The liquid is selected from hydrogen peroxide, alkali metal persulphate or perborate, peracetic acid and organic peroxide. Oxygen may be introduced into the plant as pure oxygen, or mixed with air or with hydrogen peroxide.

The oxygen in gas form is introduced into the system by injecting it into the $CO_2$ before it is compressed, or into the ammonia entering the synthesis zone, or as hydrogen peroxide into the various liquid flows upstream of the entrance to the equipment to be protected.

The passivating system using hydrogen peroxide requires, in any case, the simultaneous injection of gaseous oxygen, either as air or as pure oxygen as mentioned before.

The above-mentioned passivation systems are used to protect metal materials usually employed in industrial plants for the production of urea, such as various types of stainless steel, titanium, etc.

Besides the above-mentioned passivating agents, others have been put forward in, for example, DE-A-1800755, such as soluble ammonium nitrite, soluble sodium nitrite, and other substances not used industrially.

Nowadays the technique universally adopted to passivate metal surfaces in contact with the solutions and vapors present in the plant's various stages is to send to the synthesis reactor air and oxygen by injecting them into the $CO_2$. In some cases, besides this injection, hydrogen peroxide is also introduced into the liquid flow upstream of the equipment to be passivated.

The oxygen content injected into the $CO_2$ has a concentration of between 0.2% and 0.8% in volume and this causes some problem, of which just a few are pointed out as follows:

1. The oxygen injected as air enriches the reactor with nitrogen, with the obvious consequence that the synthesis zone is enriched with the inert gas. This creates a gas phase, the consequence of which is a reduction in urea yield in the reactor.

2. Since the $CO_2$ comes from the synthesis gas decarbonation section for the production of ammonia, it contains $H_2$, $N_2$, CO and $CH_4$ in such proportions that together with the oxygen they create explosive mixtures.

It has been found that to avoid the possibility of an explosion, the amount of oxygen injected into the $CO_2$ must be below 0.2% vol. However, under these conditions it has also been observed that the protective action over the metal surfaces is greatly reduced thus leaving them exposed to the corrosive action of both liquid and gas substances present in the various parts of the equipment.

SUMMARY OF THE INVENTION

Accordingly, an object of the present invention is to provide a process which eliminates the above drawbacks in the present state of the art. The present invention overcomes the problems arising from, on the one hand, the necessity of having oxygen in a large amount suitable for the desired passivation, and on the other hand, the necessity of avoiding the risks of explosion.

In one aspect, the present invention provides a system for the passivation of metal surfaces, and more especially metal surfaces made of stainless steel, titanium, etc., in equipment used for chemical processes where elements and compounds are formed which have a corrosive action, and in particular where temperature and pressure are higher than ambient conditions; in which system the main passivating agent is oxygen (air) combined with at least a second auxiliary agent, characterized by the fact that the latter is ozone ($O_3$).

The $O_3$ may be obtained from air or from oxygen. The amount of $O_3$ added to the oxygen may be between 0.01% and 0.1% in volume of the volume of $O_2$, the latter being by preference smaller than 0.2% in volume. A compound selected from the group consisting of hydrogen peroxide ($H_2O_2$), alkali metal peroxides, alkali earth peroxides, alkali metal persulphates or perborates, organic peroxides and acetic acid may be present together with oxygen ($O_2$) and ozone ($O_3$).

In another aspect, the present invention provides a system used in particular for the passivation of equipment used for the synthesis of urea from $NH_3$ and $CO_2$ and for the treatment of the compounds which accompany the urea synthesis, and more particularly for urea synthesis reaction and concentration equipment, for ammonium carbamate decomposition and condensation equipment, etc. Such equipment generally includes metal surfaces of Cr, Ni, stainless steel, titanium etc. The system is characterized by the fact that air including $O_3$ is injected into the feed and/or recycle of $CO_2$ and/or $NH_3$ flow and/or into further liquid and/or gas flows.

The oxidizer $O_3$ present in the $CO_2$ may vary in volume between 0.001% and 0.3%. Preferably, the oxidizer $O_3$ present in the $CO_2$ may vary between 0.01% and 0.2% in volume. In a more preferred embodiment, the $O_3$ present in the $CO_2$ may vary between 0.1% and 0.18% in volume when the $CO_2$ has a low hydrogen content, i.e., when the $CO_2$ has been obtained from the $CO_2$ absorption section with its own pre-flash in order to remove hydrogen, together with CO and nitrogen from the solution which has absorbed the $CO_2$ before entering the regeneration column. The concentration of the oxidizer $O_3$ in the liquid flows may vary between 2 and 1000 ppm.

DETAILED DESCRIPTION OF THE PREFERRED EMBODIMENTS OF THE INVENTION

In an embodiment of great industrial interest, the present invention provides a system for the passivation of metal equipment used in urea synthesis and treatment processes.

Without affecting the generality of the invention, but only as a reference to one of the most interesting and immediate applications, the present invention is disclosed in relation to plants for the industrial production of urea through the synthesis of the reactants $NH_3$ and $CO_2$. The industrial production of urea in such plants includes the formation of various compounds, besides urea, which are highly corrosive, such as more or less concentrated aqueous solutions of ammonium carbamate, ammonium carbonate, urea itself and other kinds of ionic species.

Metal surfaces of the various parts of the equipment, which come into contact with the above-mentioned compounds, are subjected to chemical corrosion which affects their integrity and efficiency.

As discussed above, the known technique for passivating metal surfaces in contact with the solutions and vapors present in the plant's various stages is to send to the synthesis reactor air and oxygen by injecting them into the $CO_2$.

Surprisingly, it has now been found that to escape the possibility of an explosion, the oxygen content may be reduced to below 0.3% vol., without affecting the passivation of the equipment, by means of adding to the passivation air small amounts of ozone ($O_3$).

The synergic action of the oxidization of air and $O_3$ permits the achievement of, among others, the following advantages:

A notable reduction of inerts in the urea synthesis reactor with the advantage of an increase in urea yield.

A reduction of the vapor phase in the reactor thus increasing the volume of the liquid phase thereby increasing its residence time.

An avoidance of the possibility of an explosion, since the $O_2$ does not create an explosive mixture with the $H_2$, CO and $CH_4$, which are present in the various stages of the plant.

The advantage of the present invention is undeniable and significant all the more since the production of $O_3$ is achieved with amply experimented conventional methods. Moreover, systems for eliminating $O_3$ from the gas inerts discharged into the atmosphere are also conventional. Therefore, where the laws for the protection of the environment forbid $O_3$ being released into the atmosphere, well-known techniques for the production of $O_3$ and its elimination are available.

The content of $O_2$ in the $CO_2$ may vary between 0.05% vol. and 0.3% vol., while the content of $O_3$ may vary between 0.01% vol. and 0.1% vol. When a compound selected from the group consisting of hydrogen peroxide ($H_2O_2$), alkali metal peroxides, alkali earth peroxides, alkali metal persulphates or perborates, organic peroxides and acetic acid is present together with $O_2$ and $O_3$, the oxygen amount can be further reduced to below 0.05% vol., f.i. between 0.01% vol. and 0.05% vol. Preferably, the third compound selected from the above group is hydrogen peroxide ($H_2O_2$).

A further advantage of the invention is that the concentration of $O_3$ may be maintained at a high level without the danger of explosion and with an appreciable increase in passivation, reducing the hydrogen ($H_2$)3 content (together with the CO, $N_2$ and $CH_4$ content) in the $CO_2$ obtained from the decarbonation plant of the ammonia synthesis gas, by preference through an additional pre-flash of the solution rich in $CO_2$ to be regenerated, before in effect it enters this regeneration stage.

The above pre-flash may be simply carried out at about 3 bar abs.

By way of illustration but without limitation of the scope of the invention, following are examples to compare the composition of the $CO_2$ sent to the synthesis reactor and of the inert gas discharged into the atmosphere, both according to the known technique for passivation and according to the invention.

A 100 t/d urea plant was used in these examples.

Composition of the $CO_2$

Comparison Example 1

Known Technique

The amount of $CO_2$ necessary for synthesis and its composition after the addition of air is as follows:

| | | | |
|---|---|---|---|
| $CO_2$ | 15610 Nm$^3$/h | 94.93% | vol. |
| $N_2$ | 491 Nm$^3$/h | 2.98 | vol. |
| $H_2$ | 164 Nm$^3$/h | 1.00 | vol. |
| $O_2$ | 98 Nm$^3$/h | 0.60 | vol. |
| CO | traces | traces | |
| $CH_4$ | 80 Nm$^3$/h | 0.49 | vol. |
| Total | 16443 Nm$^3$/h | 100.00% | vol. |

EXAMPLE 2 — INVENTION

The amount of $CO_2$ necessary for synthesis and its composition after the addition of air enriched with $O_3$ is as follows:

| | | | |
|---|---|---|---|
| $CO_2$ | 15610 Nm³/h | 96.77% | vol. |
| $N_2$ | 245 Nm³/h | 1.52 | vol. |
| $H_2$ | 164 Nm³/h | 1.02 | vol. |
| $O_2$ | 29 Nm³/h | 0.18 | vol. |
| $O_3$ | 3 Nm³/h | 0.02 | vol. |
| CO | traces | traces | |
| $CH_4$ | 80 Nm³/h | 0.49 | vol. |
| Total | 16131 Nm³/h | 100.00% | vol. |

It can be seen from the above that the amount of oxygen is appreciably reduced in the case of the invention as compared to the amount required for the known technique, while the passivating effect is equally efficient as a result of the addition of ozone ($O_3$).

Composition of the inert gas discharged into the air in the two cases:

EXAMPLE 3

| | Known technique | | | Invention | | |
|---|---|---|---|---|---|---|
| $N_2$ | 491 Nm³/h | 58.9% | vol. | 245 Nm³/h | 47.0% | vol. |
| $H_2$ | 164 Nm³/h | 19.7 | vol. | 164 Nm³/h | 31.5 | vol. |
| $O_2$ | 98 Nm³/h | 11.8 | vol. | 29 Nm³/h | 5.5 | vol. |
| $O_3$ | — | — | | 3 Nm³/h | 0.6 | vol. |
| CO | traces | — | | traces | — | |
| $CO_4$ | 80 Nm³/h | 9.6 | vol. | 80 Nm³/h | 15.4 | vol. |
| | 833 Nm³/h | 100.0% | vol. | 521 Nm³/h | 100.0% | vol. |

The possibility of an explosion of the two mixtures can easily be calculated by a conventional method, and it will be seen that the mixture according to the invention in Example 3 is outside the limits of an explosion.

The invention has been deliberately described and exemplified with reference to urea, which is one of the most difficult cases and quite emblematic as far as the phenomenon of corrosion is concerned. Of course, the invention can be applied to the majority of analogous cases, and more particularly to all chemical processes where, as for the case of urea, it is necessary to passivate with oxygen/air with or without a peroxide. According to the invention, passivation is synergically improved with the addition of $O_3$. Application to these processes remains therefore within the scope and the spirit of the invention.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

I claim:

1. A method for the passivation of stainless steel and titanium metal surfaces in equipment used for chemical processes, comprising the steps of:

feeding into the equipment feed a first oxygen-containing passivating agent; and feeding into the equipment ozone as a second passivating agent, said ozone content in said feed being at least 0.001% v/v.

2. A method according to claim 1, wherein said first passivating agent is selected from the group consisting of pure oxygen, air, oxygen-enriched air and oxygen/hydrogen peroxide mixtures.

3. A method according to claim 1, further comprising the step of introducing into the equipment metered amounts of a compound selected from the group consisting of hydrogen peroxide, alkali metal peroxides, alkali earth peroxides, alkali metal persulphates or perborates, organic peroxides and acetic acid.

4. A method for the passivation of equipment used in the synthesis and purification of urea, including area synthesis reactors, concentration equipment, ammonium carbamate decomposition and condensation equipment, said equipment comprising stainless steel and titanium metal surfaces, which method comprises the step of feeding into the equipment metered amounts of a first oxygen-containing passivating agent and of ozone, said ozone content being at least 0.001% v/v.

5. A method according to claim 4 wherein said first passivating agent is selected from the group consisting of pure oxygen, air, oxygen-enriched air and oxygen/hydrogen peroxide mixtures.

6. A method according to claim 1, wherein said first passivating agent and said ozone are dosed into a carbon dioxide stream fed into said equipment.

7. A method according to claim 6, wherein the oxygen content in said carbon dioxide stream varies from 0.05% to 0.3% v/v.

8. A method according to claim 6, wherein the ozone content in said carbon dioxide stream varies from 0.01% to 0.3% v/v.

9. A method according to claim 4, further comprising the step of introducing into the equipment feed metered amounts of a compound selected from the group consisting of hydrogen peroxide, alkali metal perioxides, alkali earth perioxides, alkali metals persulphates or perborates, organic peroxides and acetic acid.

10. A method according to claim 9, wherein said first passivating agent and said ozone are dosed into a carbon dioxide stream fed into said equipment.

11. A method according to claim 10, wherein the oxygen content in said carbon dioxide stream varies from 0.01% to 0.05% v/v.

12. A method according to claim 6, wherein the oxygen content in said carbon dioxide stream varies from 0.01% to 0.05% v/v.

13. A method according to claim 4, wherein said first passivating agent and said ozone are dosed into an ammonia or into a liquid flow fed into the equipment.

14. A method according to claim 13, wherein the ozone content in said ammonia or liquid flow varies from 2 to 1,000 ppm.

* * * * *